(12) United States Patent
Ra et al.

(10) Patent No.: US 8,871,513 B2
(45) Date of Patent: Oct. 28, 2014

(54) CULTURE MEDIUM COMPOSITION FOR CULTURING AMNION-DERIVED MESENCHYMAL STEM CELL, AND METHOD FOR CULTURING AMNION-DERIVED MESENCHYMAL STEM CELL BY USING SAME

(75) Inventors: Jeong Chan Ra, Gyeonggi-do (KR); Sung Keun Kang, Seoul (KR); Ju Yeon Seo, Gyeonggi-do (KR); Hyoeun Kim, Seoul (KR)

(73) Assignee: RNL Bio Co., Ltd., Seoul (KR)

( * ) Notice: Subject to any disclaimer, the term of this patent is extended or adjusted under 35 U.S.C. 154(b) by 0 days.

(21) Appl. No.: 13/810,334

(22) PCT Filed: Jul. 18, 2011

(86) PCT No.: PCT/KR2011/005258
§ 371 (c)(1),
(2), (4) Date: Feb. 27, 2013

(87) PCT Pub. No.: WO2012/008813
PCT Pub. Date: Jan. 19, 2012

(65) Prior Publication Data
US 2013/0164849 A1 Jun. 27, 2013

(30) Foreign Application Priority Data
Jul. 16, 2010 (KR) ........................ 10-2010-0068959

(51) Int. Cl.
 C12N 5/071 (2010.01)
 C12N 5/073 (2010.01)
 C12N 5/0775 (2010.01)

(52) U.S. Cl.
 CPC ........ *C12N 5/0605* (2013.01); *C12N 2501/115* (2013.01); *C12N 2501/33* (2013.01); *C12N 5/0668* (2013.01); *C12N 2500/14* (2013.01); *C12N 2501/39* (2013.01); *C12N 2500/32* (2013.01)
 USPC ........................... 435/405; 435/366; 435/325

(58) Field of Classification Search
 None
 See application file for complete search history.

(56) References Cited

U.S. PATENT DOCUMENTS

| 2005/0260748 A1* | 11/2005 | Chang et al. ................. 435/366 |
| 2008/0152629 A1* | 6/2008 | Edinger et al. ............... 424/93.7 |
| 2008/0159999 A1* | 7/2008 | Stefanidis .................. 424/93.21 |

FOREIGN PATENT DOCUMENTS

| KR | 10-0795708 B1 | 1/2008 |
| KR | 10-0818214 B1 | 3/2008 |
| WO | 2006019357 A1 | 2/2006 |

OTHER PUBLICATIONS

Sotiropoulou et al. "Characterization of the optimal culture conditions for clinical scale production of human mesenchymal stem cells", Stem Cells 24:462-471, 2006.*
Sorensen et al. "Comparison of culture conditions for MSCs for clinical therapy", Scandinavian Journal of Clinical & Laboratory Investigation 68(3): 192-203, 2008.*
Keating et al. "Mesenchymal stromal cells: new directions", Cell Stem Cell 10: 709-16, 2012.*
Pieternella et al. "Isolation of mesenchymal stem cells of fetal or maternal origin from human placenta", Stem Cells 22: 1338-45, 2004.*
Sigma® "Product Information: Media Supplements: ITS, SITE, SPITE", available on company's webpage, copyright 2012.*
Ahn, H., et al., "FGF2 stimulates the proliferation of human mesenchymal stem cells through the transient activation of JNK signaling", "FEBS Letters", Aug. 5, 2009, pp. 2922-2926, vol. 583, No. 17.
Battula, V., et al., "Human placenta and bone marrow derived MSC cultured in serum-free, b-FGF-containing medium express cell surface frizzled-9 and SSEA-4 and give rise to multilineage differentiation", "Differentiation", Dec. 11, 2006, pp. 279-291, vol. 75, No. 4.
Jiang, Y., et al., "Pluripotency of mesenchymal stem cells derived from adult marrow", "Nature", Jun. 20, 2002, pp. 41-49, vol. 418, No. 6893.
Jiang, Y., et al., "Multipotent progenitor cells can be isolated from postnatal murine bone marrow, muscle, and brain", "Experimental Hematology", Aug. 2002, pp. 896-904, vol. 30, No. 8.
Lin, T. et al. , "Accelerated Growth and Prolonged Lifespan of Adipose Tissue-derived Human Mesenchymal Stem Cells in a Medium Using Reduced Calcium and Antioxidants", "Stem Cells and Development", Feb. 2005, pp. 92-102, vol. 14, No. 1.
Liu, C., et al., "Cytokine interactions in mesenchymal stem cells from cord blood", "Cytokine", Dec. 21, 2005, pp. 270-279, vol. 32, No. 6.
Meuleman, N., et al., "Human marrow mesenchymal stem cell culture: serum-free medium allows better expansion than classical alpha-MEM medium", "Eur J Haematol.", Apr. 2006, pp. 309-316, vol. 76, No. 4.
Sampaolesi, M., et al., "Cell therapy of alpha-sarcoglycan null dystrophic mice through intra-arterial delivery of mesoangioblasts", "Science", Jul. 10, 2003, pp. 487-492, vol. 301, No. 5632.
Toma, J., et al., "Isolation of multipotent adult stem cells from the dermis of mammalian skin", "Nature Cell Biology", Aug. 13, 2001, pp. 778-784, vol. 3.
Verfaillie, C, "Adult stem cells: assessing the case for pluripotency", "Trends Cell Biol.", Sep. 26, 2002, pp. 502-508, vol. 12, No. 11.

* cited by examiner

*Primary Examiner* — Ruth Davis
*Assistant Examiner* — Emily Cordas
(74) *Attorney, Agent, or Firm* — Hultquist, PLLC; Steven J. Hultquist; Mary B. Grant (57) ABSTRACT

The present invention relates to a medium for culturing mesenchymal stem cells, and more particularly to a medium composition for culturing mesenchymal stem cells, which contains basal medium, L-ascorbic acid 2-phosphate, fetal bovine serum, basic fibroblast growth factor (b-FGF), non-essential amino acids (NEAAs), insulin, N-acetyl-L-cysteine, calcium chloride, and hydrocortisone, and a method of culturing mesenchymal stem cells using the same. According to the present invention, a number of mesenchymal stem cells required for stem cell therapy can be obtained in a short time, and the ability of mesenchymal stem cells to differentiate is improved so that they are useful for stem cell therapy.

2 Claims, 12 Drawing Sheets

DMEM-P Alone (5-day culture)   Mixed medium (4-day culture)
(Group 2)

FIG. 10

DMEM-P Alone (5-day culture)   Mixed medium (4-day culture)
                               (Group 2)

CULTURE MEDIUM COMPOSITION FOR CULTURING AMNION-DERIVED MESENCHYMAL STEM CELL, AND METHOD FOR CULTURING AMNION-DERIVED MESENCHYMAL STEM CELL BY USING SAME

CROSS-REFERENCE TO RELATED APPLICATIONS

This application is a U.S. national phase application under the provisions of 35 U.S.C. §371 of International Patent Application No. PCT/KR2011/005258 filed Jul. 18, 2011, which in turn claims priority of Korean Patent Application No. 10-2010-0068959 filed Jul. 16, 2010. The disclosures of such international patent application and Korean priority patent application are hereby incorporated herein by reference in their respective entireties, for all purposes.

TECHNICAL FIELD

The present invention relates to a medium for culturing mesenchymal stem cells, and more particularly to a medium composition for culturing mesenchymal stem cells, which contains basal medium, L-ascorbic acid 2-phosphate, fetal bovine serum, basic fibroblast growth factor (b-FGF), non-essential amino acids (NEAAs), insulin, N-acetyl-L-cysteine, calcium chloride, and hydrocortisone, and a method of culturing mesenchymal stem cells using the same.

BACKGROUND ART

Stem cells refer to cells having not only self-replicating ability but also the ability to differentiate into at least two types of cells, and can be divided into totipotent stem cells, pluripotent stem cells, and multipotent stem cells.

Adult stem cells are obtained by taking cells from various human organs and developing the cells into stem cells and are characterized in that they differentiate into only specific tissues. However, recently, experiments for differentiating adult stem cells into various tissues, including liver cells, were dramatically successful, which comes into spotlight.

Multipotent stem cells were first isolated from adult bone marrow (Y. Jiang et al., Nature, 418:41, 2002), and then also found in other several adult tissues (C. M. Verfaillie, Trends Cell Biol., 12:502, 2002). In other words, bone marrow is the most widely known source of stem cells, multipotent stem cells were also found in the skin, blood vessels, muscles, and brain (J. G. Toma et al., Nat. Cell Biol., 3:778, 2001; M. Sampaolesi et al., Science, 301:487, 2003; Y. Jiang et al., Exp. Hematol., 30:896, 2002). However, stem cells are very rarely present in adult tissue such as bone marrow, and such cells are difficult to culture without inducing differentiation, and thus difficult to culture in the absence of specifically screened media. Namely, it is very difficult to maintain the isolated stem cells in vitro. Meanwhile, the results of studies on the isolation of mesenchymal stem cells from fetal tissue revealed that there are abundant mesenchymal stein cells in fetal tissue. However, the use of fetal tissue as the source of cell therapeutic agents has been limited due to ethical concerns. Mesenchymal stem cells were also isolated from umbilical cord blood (UCB) as the source of fetal mesenchymal stem cells (MSCs), but numbers were very small, and they showed poor proliferation.

In recent years, it was known that mesenchymal stem cells are present in the amnion (amniotic membrane or amniotic lining membrane), i.e., the thin innermost membrane sag surrounding the placenta and a developing mammalian embryo. Thus, technologies for isolating and culturing such mesenchymal stem cells have been developed (PCT International Patent Publication No. WO 2006/019357, Korean Patent Registration Nos. 0795708 and 0818214).

However, conventional methods for culturing amnion-derived stem cells have a shortcoming in that the time taken for stem cells to proliferate is long.

Accordingly, the present inventors have made extensive efforts to develop a method capable of increasing the proliferation rate of amnion-derived stem cells while maintaining the ability to differentiate, and as a result, have found that, when amnion-derived stem cells are cultured in a medium containing DMEM-P and KSFM-P, the ability of the cells to proliferate can be increased while maintaining the ability to differentiate, thereby completing the present invention.

DISCLOSURE OF INVENTION

Technical Problem

It is an object of the present invention to provide a medium for culturing mesenchymal stem cells, which shows a high cell proliferation rate while maintaining the ability of the cells to differentiate.

Another object of the present invention is to provide a method of culturing mesenchymal stem cells using the above medium.

Technical Solution

To achieve the above objects, the present invention provides a medium composition for culturing mesenchymal stem cells, which contains basal medium, L-ascorbic acid 2-phosphate, fetal bovine serum, basic fibroblast growth factor (b-FGF), non-essential amino acids (NEAAs), insulin, N-acetyl-L-cysteine, calcium chloride, and hydrocortisone.

The present invention also provides a method for culturing mesenchymal stem cells, the method comprising culturing the mesenchymal stem cells in the above medium composition.

Other features and embodiments of the present invention will be more apparent from the following detailed descriptions and the appended claims

BEST MODE FOR CARRYING OUT THE INVENTION

In one aspect, the present invention is directed to a medium composition for culturing mesenchymal stem cells, which contains basal medium, L-ascorbic acid 2-phosphate, fetal bovine serum, basic fibroblast growth factor (b-FGF), non-essential amino acids (NEAAs), insulin, N-acetyl-L-cysteine, calcium chloride, and hydrocortisone.

In the present invention, the basal medium may be selected from the group consisting of DMEM-HG, defined keratinocyte-SFM, and a mixture thereof.

In the present invention, the medium composition may contain 0.05-1 mM of ascorbic acid 2-phosphate, 2-20% fetal bovine serum, 1-100 ng/ml of basic fibroblast growth factor (b-FGF), 1-100 μL/ml of non-essential amino acid (NEAA), 0.1-100 μg/ml of insulin, 0.2-20 mM of N-acetyl-L-cysteine, 0.01-mM of calcium chloride, and 5 ng/ml-1 μg/ml of hydrocortisone.

In the present invention, the non-essential amino acids (NEAAs) may consist of glycine, alanine, asparagines, aspartic acid, glutaminic acid, proline, and serine. In addition, the non-essential amino acids (NEAAs) may consist of 750 mg/L of glycine, 890 mg/L of alanine, 1,320 mg/L of asparagine, 1,330 mg/L of aspartic acid, 1,470 mg/L of glutaminic acid, 1,150 mg/L of proline, and 1,050 mg/L of serine.

In the present invention, the mesenchymal stem cells may be derived from amnion.

In another aspect, the present invention is directed to a method for culturing mesenchymal stem cells, the method comprising culturing the mesenchymal stem cells in the above medium composition.

In the present invention, the mesenchymal stem cells may be derived from amnion.

Amnion-derived mesenchymal stem cells used in one example of the present invention are not various kinds of cells extracted from the whole amnion isolated from the placenta, but are only amnion-derived mesenchymal stem cells.

In one example of the present invention, with respect to a method for isolating amnion-derived mesenchymal stem cells, amnion tissue was isolated from placental tissue collected during delivery, and the isolated amnion tissue was washed with sterile saline and cut as finely as possible with surgical scissors. A collagenase solution was added to and mixed well with the finely cut tissue. The mixture was placed in a flask which was then incubated in a 5% $CO_2$ incubator at 37° C. for 90 minutes to lyse the tissue. The lysed tissue was filtered through a cell strainer and centrifuged. After centrifugation, the supernatant was removed, and the cell precipitate was suspended in DMEM-P and inoculated into a T-flask, which was then incubated in a 5% $CO_2$ incubator at 37° C. for 3-4 days. Then, only mesenchymal stem cells attached to the culture flask were collected.

In one example of the present invention, amnion-derived mesenchymal stem cells showed a higher cell proliferation rate in a mixed medium of DMEM-P and KSFM-P than in DMEM-P or KSFM-P alone. Particularly, amnion-derived mesenchymal stem cells showed the highest proliferation rate in a medium consisting of DMEM-P and KSFM-P mixed at a ratio of 66:33.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Isolation of Mesenchymal Stem Cells from Amnion Tissue

Amnion tissue used in the example of the present invention was isolated from the placenta, and the isolated tissue was placed in an antibiotic-containing saline or DMEM (Dulbecco modified Eagle medium) medium and then transferred to the laboratory.

In a clean bench, 5 g of amnion tissue was washed with sterile saline, and in a Petri dish, the washed amnion tissue was cut as finely as possible with surgical scissors. A collagenase solution was added to and mixed well with the finely cut tissue. The mixture was placed in a flask which was then incubated in a 5% $CO_2$ incubator at 37° C. for 90 minutes to lyse the tissue. The lysed tissue was filtered through a cell strainer in a 50 mL tube and centrifuged. After centrifugation, the supernatant was removed, and the cell precipitate was suspended in DMEM-P and inoculated into a T-flask, which was then incubated in a 5% $CO_2$ incubator at 37° C. for 3-4 days. Then, only mesenchymal stem cells attached to the culture flask were collected.

Example 2

Figure 1:
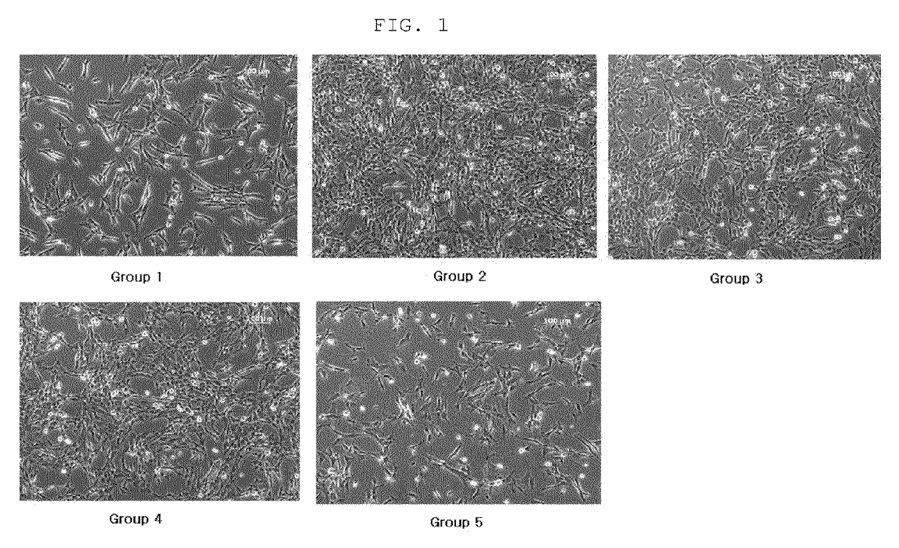
FIG. 1 shows photographs of amnion-derived mesenchymal stem cells cultured in DMEM-P, KSFM-P or a mixed medium of DMEM-P and KSFM-P for 3 days.
Figure 2:
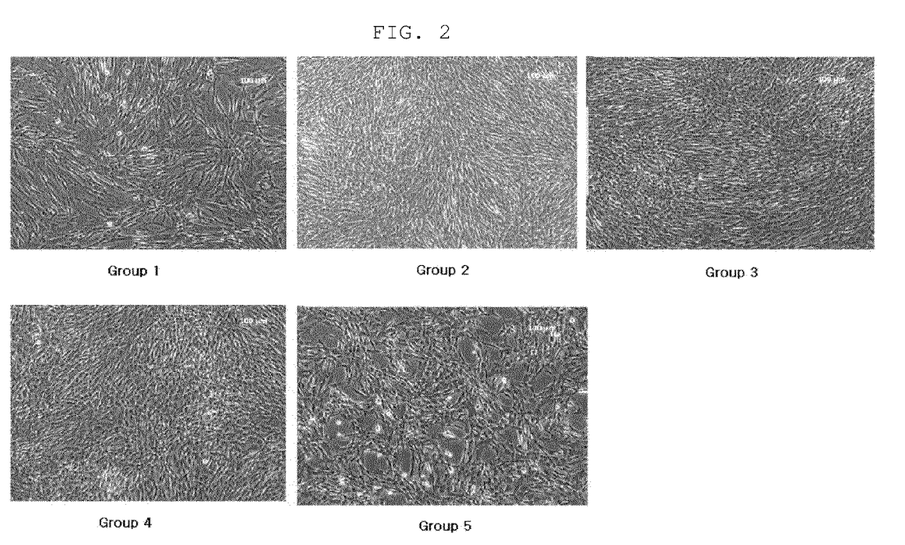
FIG. 2 photographs of amnion-derived mesenchymal stem cells cultured in DMEM-P, KSFM-P or a mixed medium of DMEM-P and KSFM-P for 4 days.
Figure 3:
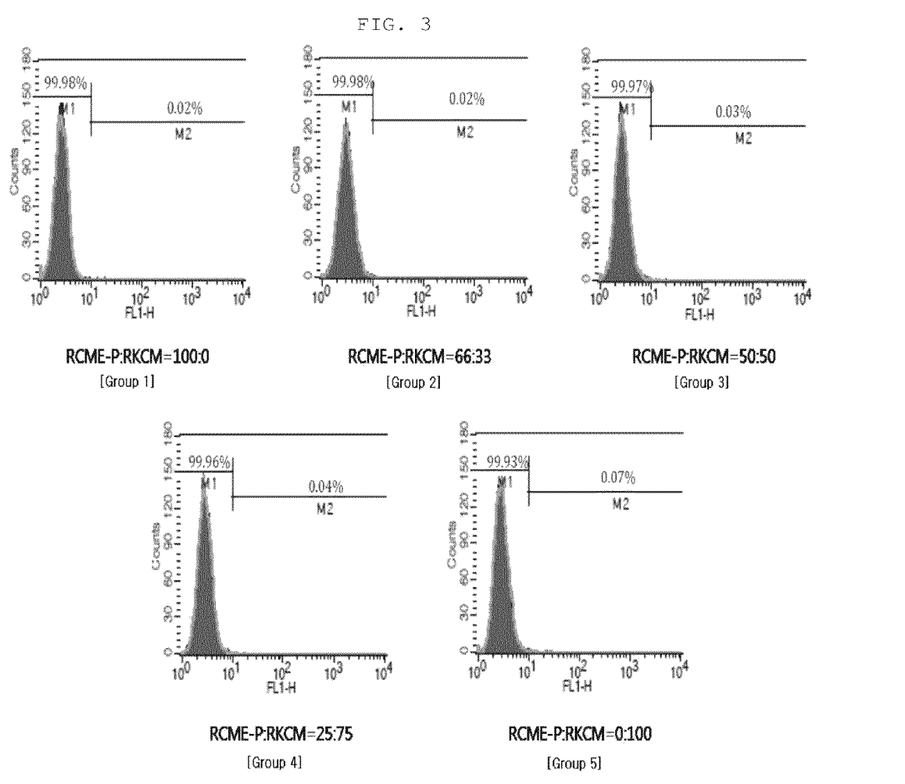
FIG. 3 shows the results of flow cytometry analysis of each group for CD31.
Figure 4:
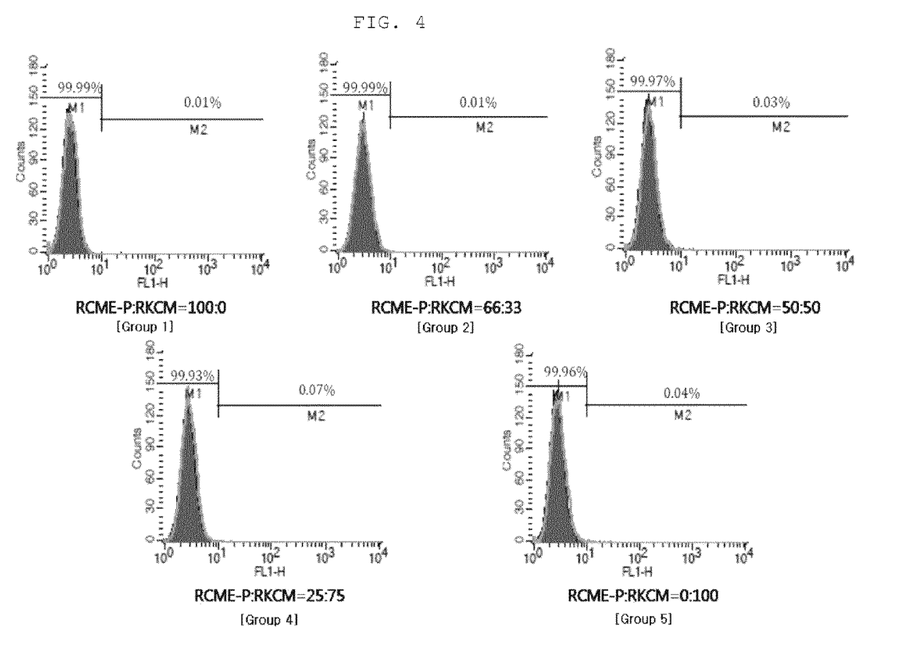
FIG. 4 shows the results of flow cytometry analysis of each group for CD34.
Figure 5:
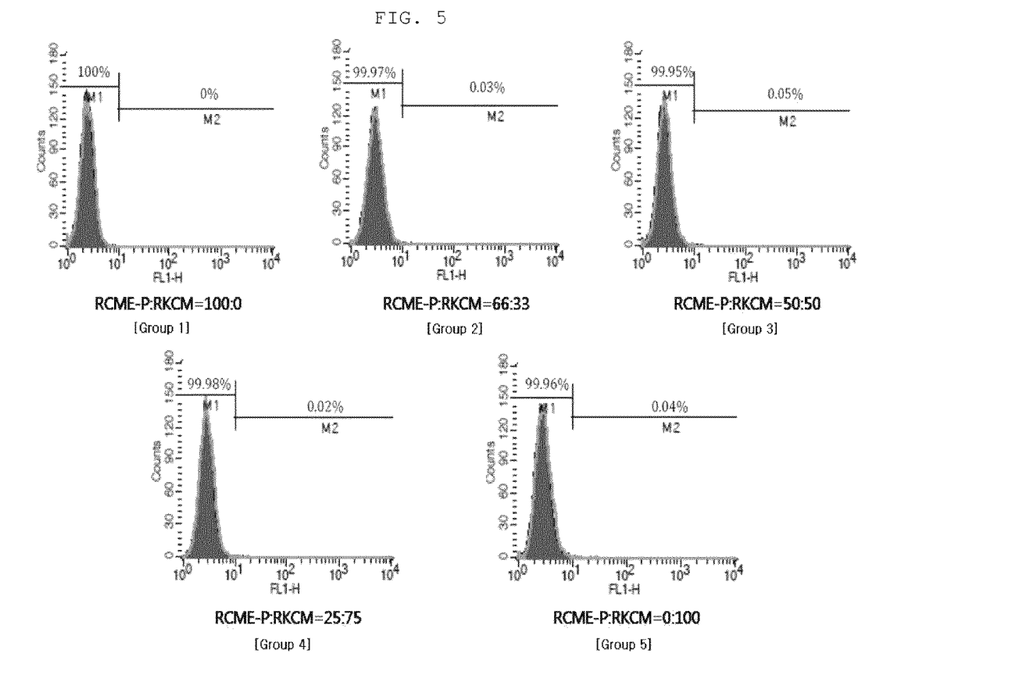
FIG. 5 shows the results of flow cytometry analysis of each group for CD45.
Figure 6:
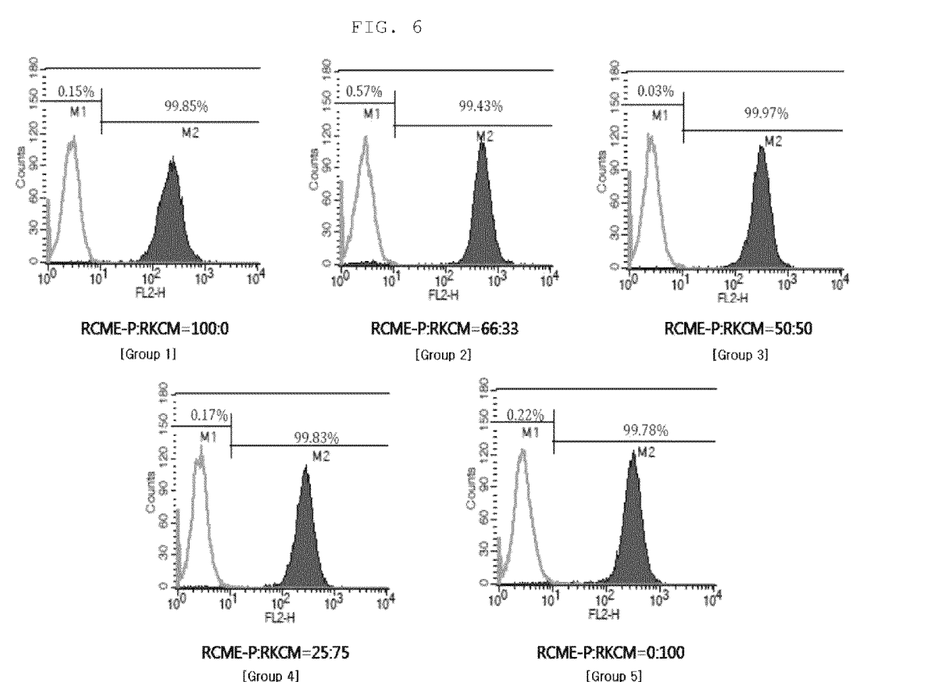
FIG. 6 shows the results of flow cytometry analysis of each group for CD29.
Figure 7:
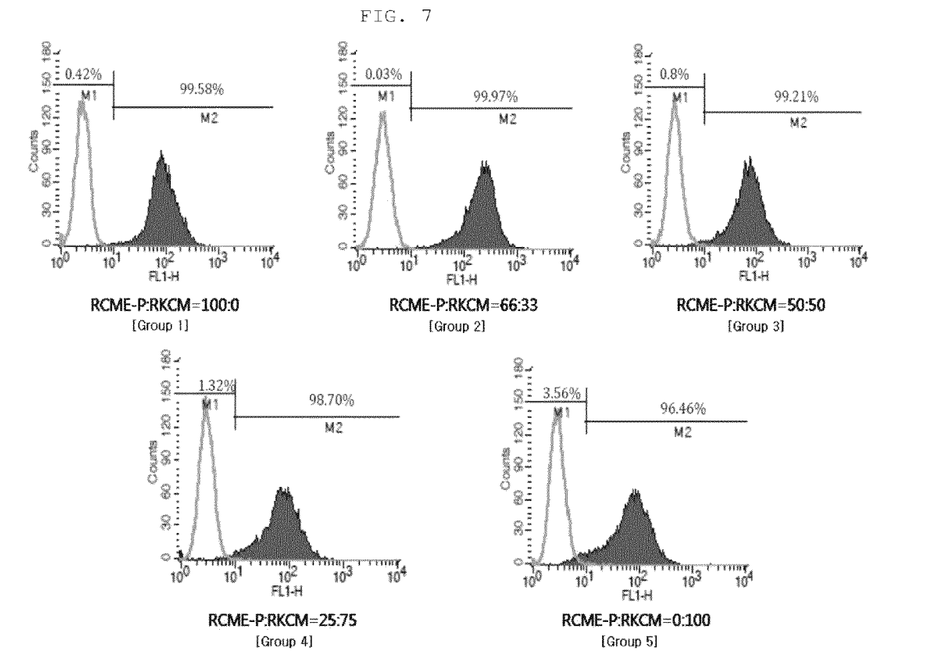
FIG. 7 shows the results of flow cytometry analysis of each group for CD44.
Figure 8:
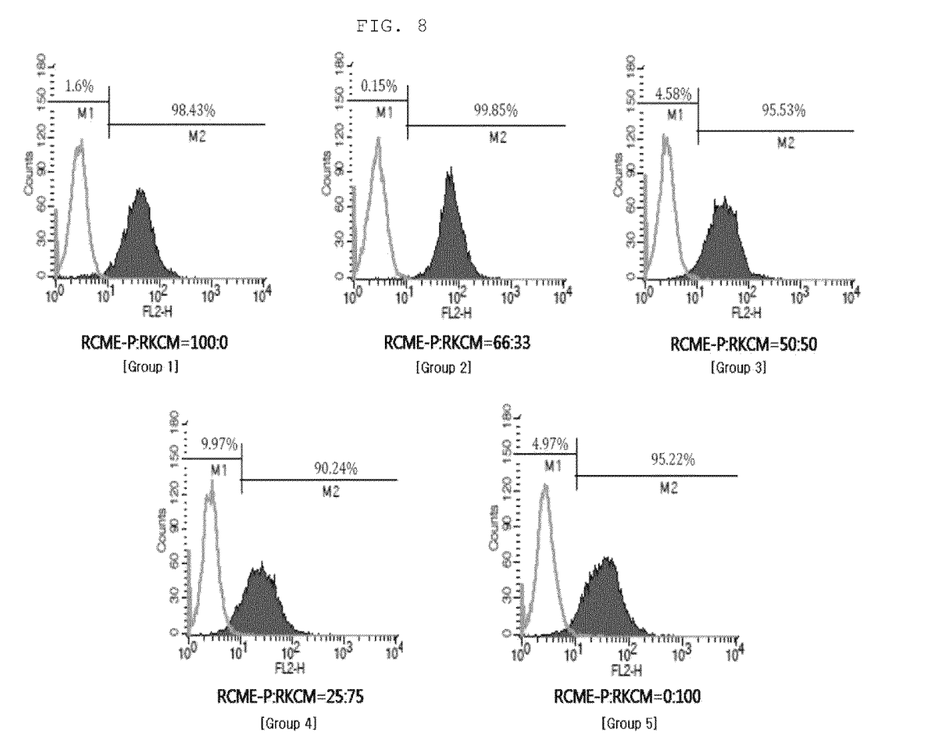
FIG. 8 shows the results of flow cytometry in each group for CD73.

Culture of Isolated Amnion Mesenchymal Stem Cells in Mixed Medium of DMEM-P and KSFM-P The amnion-derived mesenchymal stem cells obtained in Example 1 were dispensed in a T175 flask at a density of $1.0 \times 10^6$ cells and cultured in mixed media consisting of DMEM-P medium (Table 1) and KSFM-P medium (Table 3) mixed at the ratios shown in Table 4, while the media were replaced at 2-day intervals. Cell photographs taken at 3 days and 4 days of culture are shown in FIGS. 1 and 2.

TABLE 1

| Components of DMEM-P medium | | |
|---|---|---|
| Components | Purchase Source | Concentration |
| DMEM-HG | WelGENE, Inc. | |
| L-ascorbic acid 2-phosphate | Sigma-Aldrich ® | 0.2 mM |
| Fetal Bovine Serum | Invitrogen ™ | 10% |
| b-FGF | Invitrogen ™ | 10 ng/Ml |
| NEAA | Invitrogen ™ | 10 μl/Ml |

TABLE 2

Composition of NEAA

| NEAA Components | Concentration (mg/L) |
|---|---|
| Glycine | 750 |
| L-Alanine | 890 |
| L-Asparagine | 1,320 |
| L-Aspartic acid | 1,330 |
| L-Glutamic Acid | 1,470 |
| L-Proline | 1,150 |
| L-Serine | 1,050 |

TABLE 3

Components of KSFM-P medium

| Components | Purchase Source | Concentration |
|---|---|---|
| Defined Keratinocyte-SFM | Invitrogen ™ | |
| L-ascorbic acid 2-phosphate | Sigma-Aldrich ® | 0.2 mM |
| Insulin | Millipore | 5 µg/Ml |
| N-acetyl-L-cysteine | Sigma-Aldrich ® | 2 mM |
| Calcium chloride | Sigma-Aldrich ® | 0.09 mM |
| Hydrocortisone | Sigma-Aldrich ® | 74 ng/Ml |
| Fetal Bovine Serum | Invitrogen ™ | 5% |

TABLE 4

Mixing ratio of DMEM-P and KSFM-P

| Groups | DMEM-P | KSFM-P |
|---|---|---|
| 1 | 100 | 0 |
| 2 | 66 | 33 |
| 3 | 50 | 50 |
| 4 | 25 | 75 |
| 5 | 0 | 100 |

At 4 days of culture, the amnion-derived mesenchymal stem cells were washed with HBSS buffer, and then incubated in TrypLE™ Express (Gibco®) or 0.25% Trypsin-EDTA at 37° C. for 10 minutes. FBS-containing medium was added thereto to inactivate the trypsin, and then the number of the resulting amnion-derived mesenchymal stem cells was counted.

As a result, as can be seen in Table 4 and FIGS. 1 and 2, the amnion-derived stem cells grew much faster in a mixed medium of DMEM-P medium and KSFM-P medium than in DMEM-P medium or KSFM-P medium alone, and the number of the cells at days of culture was also significantly larger when the cells were cultured in the mixed medium of DMEM-P medium and KSFM-P medium.

As shown in Table 5 below, a medium of Group 2 consisting of DMEM-P medium and KSFM-P medium mixed at a ratio of 66:33 showed the highest cell proliferation rate. Thus, the mixed medium of Group 2 was used in subculture.

TABLE 5

Change in cell number as a function of ratio of mixing of media

| Groups | DMEM-P:KSFM-P | The number of cells |
|---|---|---|
| 1 | 100:0 | $1.2 \times 10^7$ |
| 2 | 66:33 | $3.7 \times 10^7$ |
| 3 | 50:50 | $2.4 \times 10^7$ |
| 4 | 25:75 | $2.0 \times 10^7$ |
| 5 | 0:100 | $1.4 \times 10^7$ |

Example 3

Immunological Characteristics of Amnion-Derived Mesenchymal Stem Cells Cultured in Mixed Medium Flow Cytometry Analysis of Surface Antigen Expression The amnion-derived mesenchymal stem cells cultured in the mixed culture in Example 2 were characterized with CD series antigen markers. FACS analysis were performed using CD29 (mononuclear cell marker), CD31 (endothelial cell and stem cell marker), CD34 (hematopoietic stem cell marker), CD44, CD45 (PTPR, ASV, leukocyte marker) and CD73.

The amnion-derived mesenchymal stem cells obtained in Example 1 were washed with PBS and treated with trypsin, after which the cells were collected and centrifuged at 1500 rpm for 5 minutes. The supernatant was removed, and the cells were incubated in a blocking buffer solution (5% serum (normal goat serum+normal horse serum)) at 4° C. for 60 minutes, followed by centrifugation at 1500 rpm for 5 minutes. After the supernatant has been removed, the cells were suspended in PBS and dispensed in each well at a density of $1 \times 10^5$ cells corresponding to the number of negative control and CD antigen markers. R-phycoerythrin (PE)/FITC (fluorescein isothiocyanate)-conjugated mouse anti-human monoclonal antibody was added to each well and incubated at 4° C. for 40 minutes, followed by centrifugation at 1500 rpm for 3 minutes. The supernatant was removed, and the cells were washed with PBS and centrifuged at 1500 rpm for 3 minutes. Then, the process of removing the supernatant, washing the cells with PBS and centrifuging the cells at 1500 rpm for 3 minutes was repeated once more. After the supernatant has been removed, the cells were analyzed using a flow cytometer.

As a result, the amnion-derived mesenchymal stem cells of each group were all immunologically positive for CD29, CD44 and CD73 and immunologically negative for CD31, CD34 and CD45 (see FIGS. 3 to 8).

Example 4

Comparison of Proliferation Ability Between Amnion-Derived Mesenchymal Stem Cells Subcultured in Mixed Medium The cells cultured in Example 1 were subcultured at a concentration of $1.0 \times 10^6$ cells/T175 flask, and the abilities of passage 1 (P1) and passage 2 (P2) cells to proliferate were examined.

The subculture was performed under the same conditions as those of Example 1.

Figure 9:
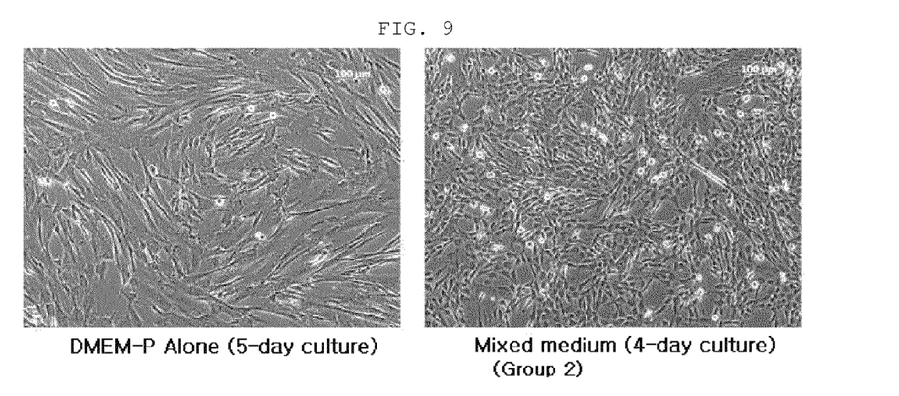
FIG. 9 is a set of photographs showing amnion mesenchymal stem cells cultured in a mixed medium of DMEM-P and KSFM-P (Group 2) in passage 1 (P1).

As a result, the P1 cells of the group cultured in DMEM-P medium alone (Group 1) were measured to be $5.4 \times 10^6$ cells after 5 days of culture, whereas the P1 cells of the group cultured in the mixed medium of DMEM-P and KSFM-P (66:33) (Group 2) were measured to be $1.25 \times 10^7$ cells after 4 days of culture, suggesting that the cells showed a significantly high ability to proliferate in the mixed medium (see FIG. 9).

Figure 10:
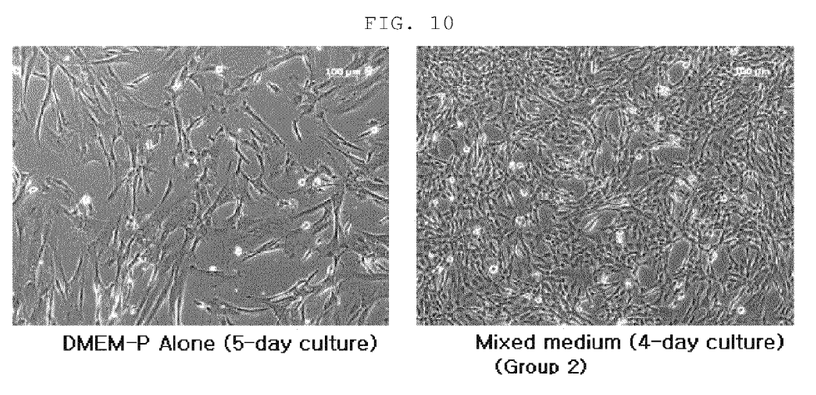
FIG. 10 is a set of photographs showing amnion mesenchymal stem cells cultured in a mixed medium of DMEM-P and KSFM-P (Group 2) in passage 2 (P2).

The P2 cells of the group cultured in DMEM-P medium alone (Group 1) were measured to be $3.4\times10^6$ cells after 4 days of culture, and thus the number of the proliferated cells decreased compared to the number of the P1 cells. However, the P2 cells of the group cultured in the mixed medium of DMEM-P and KSFM-P (66:33) (Group 2) were measured to be $1.38\times10^7$ cells after 4 days of culture, and thus the number of the P2 cells increased compared to the P1 cells (see FIG. 10).

Example 5

Comparison of Immunological Characteristics Between Amnion-Derived Mesenchymal Stem Cells Subcultured in Mixed Medium In the same manner as Example 2, P1 and P2 cells were obtained by subculture using each of DMEM-P medium alone and a mixed medium of DMEM-P and KSFM-P (66:33). The immunological characteristics of the P1 and P2 cells were examined, and as a result, the amnion-derived mesenchymal stem cells of each group were all immunologically positive for CD29, CD44, CD73, CD90, CD105 and HLA-ABC and immunologically negative for CD31, CD34, CD45 and HLA-DR.

Example 6

Quantification of Osteogenic Differentiation of Amnion-Derived Mesenchymal Stem Cells Cultured in Mixed Medium The amnion-derived mesenchymal stem cells cultured in each of DMEM-P medium alone and the mixed medium of DMEM-P/KSFM-P in Example 1 were cultured in osteogenesis induction medium (nonhematopoietic OsteoDiff medium, Miltenyi® Biotec) for 18 days (37° C.; 5% $CO_2$; medium replacement cycle: 3-4 days) to induce differentiation into bone cells, and the differentiation medium was replaced with fresh medium at 2-day intervals. The differentiation of the amnion-derived mesenchymal stem cells into bone cells was performed in each of a normoxic state and a hypoxic state (1-5%) under the conditions shown in Table 6 below.

Figure 11:
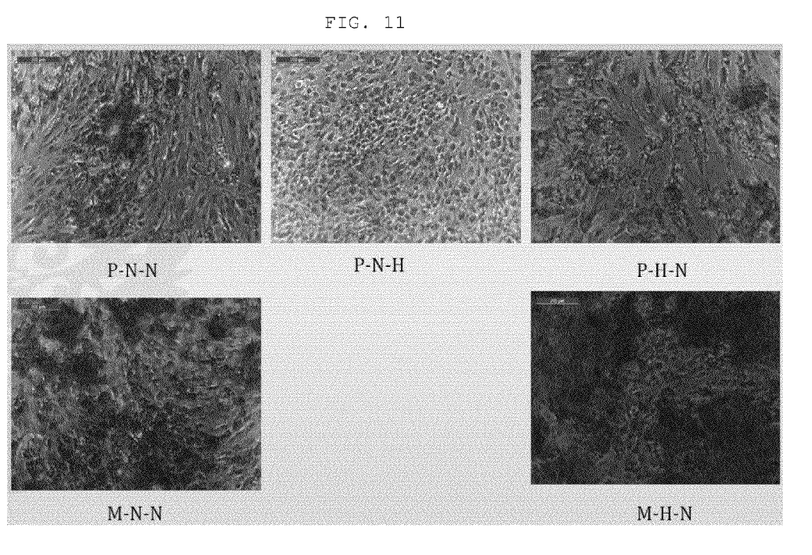
FIG. 11 shows the results of analyzing the osteogenic differentiation of amnion mesenchymal stem cells, cultured in a mixed medium of DMEM-P and KSFM-P (Group 2), using Alizarin red S staining under various conditions.
Figure 12:
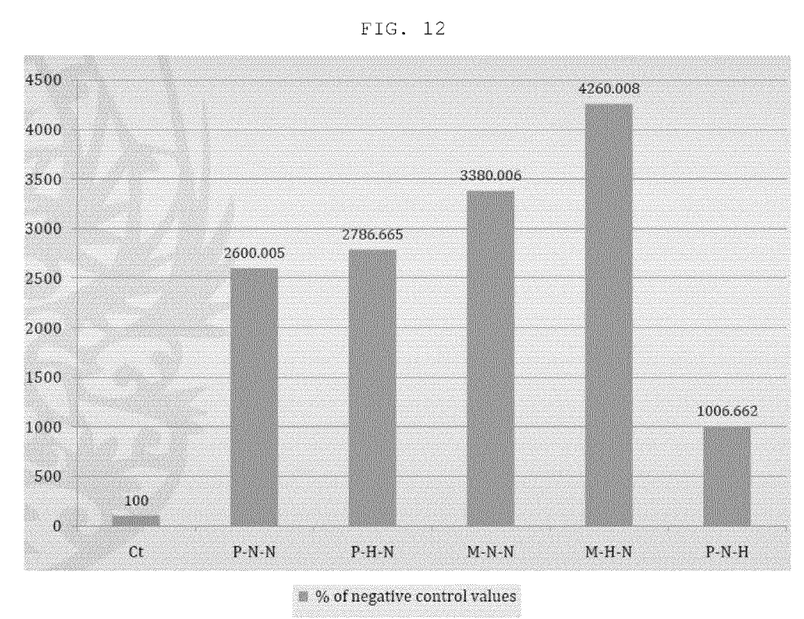
FIG. 12 is a graph showing a comparison between the quantified concentration of Alizarin red S in amnion-derived mesenchymal stem cells, cultured in DMEM-P or a mixed medium (Group 2) and differentiated into bone cells under various conditions, and that in a control group (whose osteogenic differentiation was not induced).

At 18 days after the start of culture, it was confirmed by Alizarin red S staining that the amnion-derived mesenchymal stem cells differentiated into osteogenic cells. In addition, the cells cultured in the mixed medium (Group 2) differentiated at a rate higher than the cells cultured in DMEM-P medium alone, and the cells (M-H-N) cultured in the hypoxic state showed a higher ability to differentiate (see FIGS. 11 and 12).

TABLE 6

| P2 Culture Conditions | | P3 Differentiation | | Alizarin Red | |
|---|---|---|---|---|---|
| Culture Media | Incubation | Conditions Incubation | $OD_{405}$ | Concentration | Symbols |
| DMEM-P | Normoxia | Normoxia | 0.125 | 4.20712 | P—N—N |
|  | Normoxia | Hypoxia | 0.045333 | 1.6289 | P—N—H |
|  | Hypoxia | Normoxia | 0.134333 | 4.509159 | P—H—N |

TABLE 6-continued

| P2 Culture Conditions | | P3 Differentiation | | Alizarin Red | |
|---|---|---|---|---|---|
| Culture Media | Incubation | Conditions Incubation | $OD_{405}$ | Concentration | Symbols |
| DMEM-P+ KSFM-P- Mix | Normoxia Hypoxia | Normoxia Normoxia | 0.164 0.208 | 5.469256 6.893204 | M—N—N M—H—N |

INDUSTRIAL APPLICABILITY

According to the present invention, a number of mesenchymal stem cells required for stem cell therapy can be obtained in a short time, and the ability of mesenchymal stem cells to differentiate is improved so that they are useful for stem cell therapy.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for culturing amnion-derived mesenchymal stem cells, the method comprising culturing the mesenchymal stem cells in a medium composition comprising:
    (i) Dulbecco's modified Eagle medium-P (DMEM-P) containing Dulbecco's modified Eagle medium-high glucose (DMEM-HG), 0.2 mM of L-ascorbic acid 2-phosphate, 10% fetal bovine serum, 10 ng/ml of basic fibroblast growth factor (b-FGF), 10 µl/ml of non-essential amino acid (NEAA); and
    (ii) keratinocyte serum free medium-P (KSFM-P) containing Defined Keratinocyte-SFM, 0.2 mM of L-ascorbic acid 2-phosphate, 5 µg/ml of insulin, 2 mM of N-acetyl-L-cysteine, 0.09 mM of calcium chloride, 74 ng/ml of hydrocortisone, 5% fetal bovine serum,
    wherein the non-essential amino acid (NEAA) consists of 750 mg/L of glycine, 890 mg/L of L-alanine, 1,320 mg/L of L-asparagine, 1,330 mg/L of L-aspartic acid, 1,470 mg/L of L-glutamic acid, 1,150 mg/L of L-proline, and 1,050 mg/L of L-serine, and the volume ratio of DMEM-P:KSFM-P is 66:33.

2. A method for improving the ability of amnion-derived mesenchymal stem cells to proliferate, the method comprising culturing the mesenchymal stem cells in a medium composition comprising:
    (i) Dulbecco's modified Eagle medium-P (DMEM-P) containing Dulbecco's modified Eagle medium-high glucose (DMEM-HG), 0.2 mM of L-ascorbic acid 2-phosphate, 10% fetal bovine serum, 10 ng/ml of basic fibroblast growth factor (b-FGF), 10 µl/ml of non-essential amino acid (NEAA); and
    (ii) keratinocyte serum free medium-P (KSFM-P) containing Defined Keratinocyte-SFM, 0.2 mM of L-ascorbic acid 2-phosphate, 5 µg/ml of insulin, 2 mM of N-acetyl-L-cysteine, 0.09 mM of calcium chloride, 74 ng/ml of hydrocortisone, 5% fetal bovine serum,
    wherein the non-essential amino acid (NEAA) consists of 750 mg/L of glycine, 890 mg/L of L-alanine, 1,320 mg/L of L-asparagine, 1,330 mg/L of L-aspartic acid, 1,470 mg/L of L-glutamic acid, 1,150 mg/L of L-proline, and 1,050 mg/L of L-serine, and the volume ratio of DMEM-P:KSFM-P is 66:33.

* * * * *

UNITED STATES PATENT AND TRADEMARK OFFICE
CERTIFICATE OF CORRECTION

Page 1 of 1

PATENT NO.         : 8,871,513 B2
APPLICATION NO.    : 13/810334
DATED              : October 28, 2014
INVENTOR(S)        : Jeong Chan Ra

It is certified that error appears in the above-identified patent and that said Letters Patent is hereby corrected as shown below:

In the Specification

Column 1, line 58: "stein" should be -- stem --.

Column 1, line 63: "but numbers" should be -- but their numbers --.

Signed and Sealed this
Sixth Day of January, 2015

Michelle K. Lee
*Deputy Director of the United States Patent and Trademark Office*